US00PP33155P2

(12) United States Plant Patent
Bradford et al.

(10) Patent No.: US PP33,155 P2
(45) Date of Patent: Jun. 15, 2021

(54) PLUM TREE NAMED 'PLUMRED IV'

(50) Latin Name: *Prunus salicina*
Varietal Denomination: Plumred IV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/974,333

(22) Filed: Jan. 4, 2021

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 5/0862
See application file for complete search history.

(56) References Cited

U.S. PATENT DOCUMENTS

PP18,687 P2 4/2008 Bradford
PP19,537 P2 12/2008 Bradford

*Primary Examiner* — Kent L Bell

(57) ABSTRACT

The present invention relates to a plum tree, *Prunus salicina*, and more particularly to a new and distinct variety broadly characterized by a large size, vigorous, hardy, and moderately productive tree. Being self-unfruitful, the present variety requires cross pollination from an apricot, interspecific, or plum that blooms during the early season, such as 'Blackred I' interspecific tree (U.S. Plant Pat. No. 19,537). The present variety produces a heavy amount of flowers that produce an abundance of pollen to entice good bee activity to facilitate pollination. The fruit matures under the ecological conditions described during early June, with first picking on Jun. 8, 2020. The fruit is medium in size, a solid dark purplish red skin color, full red to pink in flesh color, clingstone in type, oblate in shape, firm in texture, juicy, sweet, and very good in flavor.

1 Drawing Sheet

Botanical classification: *Prunus salicina.*
Varietal denomination: 'PLUMRED IV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'Plumred IV'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2008 one such house containing 'Plumsweet VI' interspecific tree (U.S. Plant Pat. No. 18,687) was crossed by us in this manner. To pollinate this interspecific tree, we selected bouquets from several sources of plum trees without keeping specific written details. Upon reaching maturity the fruit from this interspecific tree was harvested, and the seeds were removed, cracked, stratified and germinated as a group with the label "H22". They were grown as seedlings on their own root in our greenhouse and upon reaching dormancy transplanted to a cultivated area of our experimental orchard located near Le Grand, Calif. in Merced County (San Joaquin Valley). During the Summer of 2012 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent 'Plumsweet VI' interspecific tree (U.S. Plant Pat. No. 18,687), by being self-unfruitful and by producing fruit that is firm, sweet, oblate in shape, clingstone in type, and red to pink in flesh color, but is quite distinguished therefrom by producing fruit that is larger in size, fully red in skin color instead of red with heavy greenish yellow mottling, and that ripens a few days earlier.

The present variety is most similar to 'Blackred I' interspecific tree (U.S. Plant Pat. No. 19,537), by blooming in the early season, by being self-unfruitful, and by producing fruit that is oblate in shape, firm in texture, fairly red in flesh color, and clingstone in type, but is distinguished therefrom by producing fruit that is dark red instead of black in skin color, that is a little sweeter in flavor, that is somewhat larger in size, and that matures about eight days later.

SUMMARY OF VARIETY

The present plum variety is characterized by a large size, vigorous, hardy, and moderately productive tree. Being self-unfruitful, the present variety requires cross pollination from an apricot, interspecific, or plum that blooms during the early season, such as 'Blackred I' interspecific tree (U.S. Plant Pat. No. 19,537). The present variety produces a heavy amount of flowers that produce an abundance of pollen to entice good bee activity to facilitate pollination. The fruit matures under the ecological conditions described during early June, with first picking on Jun. 8, 2020. The fruit is medium in size, a solid dark purplish red skin color, full red to pink in flesh color, clingstone in type, oblate in shape, firm in texture, juicy, sweet, and very good in flavor.

DRAWING

The accompanying photograph consists of four whole fruits positioned to display the characteristics of the skin color and form, one divided fruit to reveal the flesh and stone, a tip shoot growth, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jun 12, 2020, on the original tree during its eighth growing season. The flower and bud descriptions were developed during the previous blooming season. All major color code designations are by reference to the Inter-Society Color Council, National Bureau of Standards. Common color names are also used occasionally.

PARENTAGE

Seed parent: 'Plumsweet VI' (U.S. Plant Pat. No. 18,687) interspecific tree.

Pollen parent: Unknown plum.

TREE

Size: Large, reaching and maintaining a height of 13' [3.96 m.] and a spread of 9' [2.74 m.] after eight growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Half hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Moderately productive, thinning usually necessary.

Fertility: Self-unfruitful, requiring cross pollination by a suitable early seasonal blooming apricot, interspecific, or plum, such as 'Blackred I' interspecific tree (U.S. Plant Pat. No. 19,537).

Bearing: Moderate, weather dependent, as a few light crops have been observed following rainy blooming seasons.

Trunk:

*Size.*—Medium, reaching a maximum diameter of 6¾" [171.5 mm.] after the eighth growing season.

*Texture.*—Medium to shaggy.

*Bark color.*—A Grayish brown [61. gy.Br] and Moderate brown [58. m.Br] variegation with Dark brown [59. d.Br] crevices present.

*Lenticels.*—Approximate Number Per Square Inch: 8. Color: Brownish orange [54. brO]. Average Size: ¼" [6.4 mm.] in length. The width is typically one fourth as much as the length. Shape: Elongated.

Branches:

*Size.*—Medium, scaffold diameter is 4½" [114.3 mm.] measured 12" above the crotch, limb diameter is 1¾" [44.5 mm.] measured 12" above the first fork.

*Texture.*—Medium on first and second year wood, increasing roughness with age.

*Color.*—1st Year Wood Topside: Grayish red [19. gy.R]. 1st Year Wood Underside: Brilliant yellow green [116. brill.YG]. Older Wood: A Light grayish brown [60. l.gy.Br] and Grayish brown [61. gy.Br] variegation.

*Lenticels.*—Number Per Square Inch: About 10 on second year wood. Color: Light grayish brown [60. l.gy.Br]. Average Size: Medium, 1/16" [1.6 mm.] in length. The width is typically one fourth as much as the length. Shape: Elongated.

Leaves:

*Size.*—Medium to large. Average Length: 4½" [114.3 mm.]. Average Width: 2 1/16" [52.4 mm.].

*Arrangement.*—Alternate.

*Thickness.*—Medium.

*Form.*—Elliptical.

*Apex.*—Acuminate.

*Base.*—Acute with an average base angle of 75 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 11/16" [17.5 mm.]. Average Thickness: 1/16" [1.6 mm.]. Color: Vivid yellow green [115. v.YG].

*Stipules.*—Number: Mostly 2 per leaf, up to 6 per growing tip. Average Length: 3/16" [4.8 mm.]. Color: Moderate yellow green [120. m.YG] becoming Dark grayish yellow [91. d.gy.Y] with age.

*Glands.*—Number: Mostly 2 per leaf. Position: Alternate, positioned at base of leaf blade. Form: Globose. Size: Small, 1/32" [0.8 mm.] in diameter. Color: Light yellow green [119. l.YG]. Leaf buds: Pointed.

Flower buds:

*Hardiness.*—Hardy, with respect to central California blooming season.

*Diameter.*—Typically 3/16" [4.8 mm.] 1 week before bloom.

*Length.*—Typically ⅜" [9.5 mm.] 1 week before bloom.

*Form.*—Free, not touching.

*Surface.*—Slightly pubescent.

*Tip color.*—White [263. White].

Flowers: Perfect, complete, perigynous, usually a single pistil, about thirty stamens, five sepals and petal locations alternately positioned.

*Average flower diameter.*—1⅛" [28.6 mm.].

*Average flower depth.*—⅜" [9.5 mm.] when fully open.

*Number of petals.*—Five, no double blossoms observed.

*Petal shape.*—Oval.

*Petal margin.*—Entire, somewhat wavy.

*Petal arrangement.*—Not overlapping at full bloom.

*Average petal diameter.*—9/16" [14.3 mm.].

*Average petal length.*—⅝" [15.9 mm.].

*Petal apex.*—Rounded.

*Petal base.*—Obtuse.

*Petal color.*—White [263. White] on both sides.

*Anther color.*—Light orange yellow [70. l.OY] with Moderate reddish orange [37. m.rO] edges.

*Pollen production.*—Strong, enticing to bees.

*Stigma color.*—Light yellow green [119. l.YG].

*Stigma position.*—Located slightly above the average anther position.

*Stamen position.*—Typically located about 1/32" [0.8 mm] below the petals.

*Sepal color.*—Vivid yellow green [115. v.YG] on the outside, Brilliant yellow green [116. brill.YG] on the inside.

*Sepal outer surface.*—Slightly pubescent.

*Sepal length.*—3/16" [4.8 mm.].

*Sepal width.*—⅛" [3.2 mm.].

*Sepal apex.*—Rounded to elliptical to match the width and length.

*Sepal margin.*—Fairly smooth.

*Average pistil length.*—11/16" [17.5 mm.].

*Average stamen length.*—9/16" [14.3 mm.].

*Ovary.*—Smooth.

*Fragrance.*—Moderate.

*Pollen production.*—Strong, bee enticing.

*Bloom density.*—Heavy.

*Number per cluster.*—2 to 7, mostly 2.

*Blooming period.*—Early, about three days before 'Blackred I' (U.S. Plant Pat. No. 19,537) interspecific tree.

*Onset of bloom.*—One percent on Feb. 17, 2020.

*Date of full bloom.*—Feb. 25, 2020.

*Duration of bloom.*—One to two weeks, dependent on ambient temperature.

FRUIT

Maturity when described: Firm ripe, Jun. 12, 2020.

Date of first picking: Jun. 8, 2020.

Date of last picking: Jun. 20, 2020.

Size: Fairly uniform, medium.

*Average diameter axially.*—2¼" [57.2 mm.].

*Average diameter across cheek plane.*—2½" [63.5 mm.].

*Average diameter across suture plane.*—2 9/16" [65.1 mm.].

*Typical weight.*—5.8 ounces [164 grams].

Form: Fairly uniform, oblate, symmetrical, compressed axially.

*Longitudinal section form.*—Oblate.

*Axial view form.*—Round.

Suture: An inconspicuous shallow trough extending from the base just to the apex.

Ventral surface: Rounded, lipped on both sides very slightly.

Lips: Equal.

Cavity: Flaring.

*Depth.*—5/16" [7.9 mm.].

*Breadth.*—1⅛" [28.6 mm.].

Base: Truncate, slightly cordate if viewed parallel to the suture.

Apex: Rounded to slightly truncate.

Pistil point: A conspicuous Light yellowish brown [76. l.yBr] dot.

Stem: Medium.

*Average length.*—7/16" [11.1 mm.].

*Average width.*—3/32" [2.4 mm.].

Skin:

*Thickness.*—Medium.

*Surface.*—Smooth.

*Tenacity.*—Tenacious to the flesh.

*Astringency.*—Slight.

*Tendency to crack.*—None observed.

*Color.*—Dark purplish red [259. d.pR] smoothly blending to Dark red [16. d.R] with heavy, very fine Light yellowish brown [76. l.yBr] freckling throughout.

Flesh:

*Color.*—Deep red [13. deep R] close to the skin smoothly blending to Dark pink [6. d.Pk] towards the stone with Light yellowish pink [28. l.yPk] fibers throughout.

*Surface of pit cavity.*—Covered with Moderate red [15. m.R] fibers when twisted from the stone.

*Amygdalin.*—Moderate.

*Juice.*—Abundant, rich.

*Texture.*—Firm, tough, meaty.

*Fibers.*—Abundant.

*Ripens.*—Fairly evenly, slightly earlier toward the shoulder.

*Flavor.*—A delicious blend of acid and sugar, typically 18 brix.

*Aroma.*—Very slight.

*Eating quality.*—Very good.

STONE

Type: Clingstone.

Form: Oval.

Hilum: Narrow.

Base: Slightly oblique.

Apex: Obtuse.

Tip: About 1/16" [1.6 mm.] in length.

Sides: Equal.

Surface: Very rough with one furrow on each side.

External color of stone: Light yellowish brown [76. l.yBr].

Pit wall color when cracked: Light yellowish brown [76. l.yBr].

Cavity surface color: Strong yellowish brown [74. s.yBr].

Average pit wall thickness: 1/16" [1.6 mm.].

Average length: ⅝" [15.9 mm.].

Average width: 9/16" [14.3 mm.].

Average breadth: 5/16" [7.9 mm.].

Tendency to split: None observed.

Kernel:

*Form.*—Oval.

*Skin color.*—Pale yellow [89. p.Y].

*Pellicle color.*—Light grayish yellowish brown [79. l.gy.yBr].

*Vein color.*—Very few Light yellowish brown [76. 1.yBr] veins.
*Taste.*—Bitter.
*Viable.*—Yes.
*Average length.*—7/16" [11.1 mm.].
*Average width.*—3/8" [9.5 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Blackred I' interspecific tree (U.S. Plant Pat. No. 19,537), by blooming in the early season, by being self-unfruitful, and by producing fruit that is oblate in shape, firm in texture, fairly red in flesh color, and clingstone in type, but is distinguished therefrom by producing fruit that is dark red instead of black in skin color, that is a little sweeter and better in flavor, that is somewhat larger in size, and that matures about eight days later.

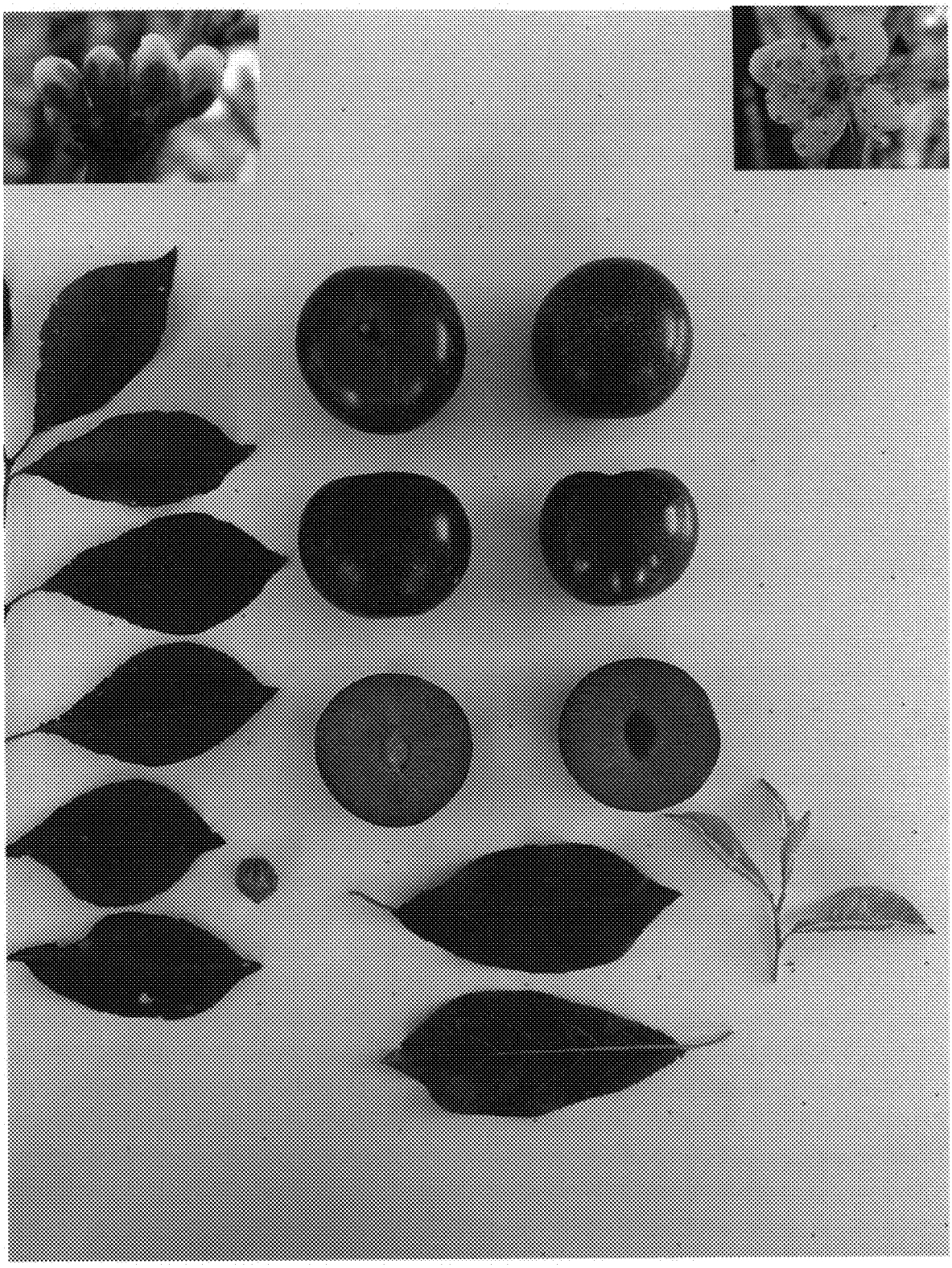

* * * * *